United States Patent [19]

Kelkenberg et al.

[11] Patent Number: 5,009,814
[45] Date of Patent: Apr. 23, 1991

[54] USE OF N-POLYHYDROXYALKYL FATTY ACID AMIDES AS THICKENING AGENTS FOR LIQUID AQUEOUS SURFACTANT SYSTEMS

[75] Inventors: Heike Kelkenberg, Gladbeck; Wulf Ruback, Recklinghausen; Klaus Engel, Duisburg, all of Fed. Rep. of Germany

[73] Assignee: Hüls Aktiengesellschaft, Marl, Fed. Rep. of Germany

[21] Appl. No.: 262,257

[22] Filed: Oct. 20, 1988

Related U.S. Application Data

[63] Continuation of Ser. No. 149,479, Jan. 28, 1988, abandoned.

[30] Foreign Application Priority Data

Apr. 8, 1987 [DE] Fed. Rep. of Germany ....... 3711776

[51] Int. Cl.$^5$ .......................... C11D 3/32; C11D 17/00
[52] U.S. Cl. ................ 252/548; 252/174.21; 252/174.22; 252/DIG. 5; 252/DIG. 13; 252/DIG. 14; 424/70
[58] Field of Search ............ 252/548, 529, 174.21, 252/174.22, DIG. 13, DIG. 14, DIG. 5, 544; 424/70

[56] References Cited

U.S. PATENT DOCUMENTS

| | | | |
|---|---|---|---|
| 2,662,073 | 12/1953 | Mehltretter | 260/102 |
| 2,703,798 | 3/1955 | Schwartz | 260/211 |
| 2,831,815 | 4/1958 | Klisch | 252/152 |
| 2,870,091 | 1/1959 | Tomlinson | 252/137 |
| 2,965,576 | 12/1960 | Wilson | 252/137 |
| 3,644,204 | 2/1972 | Heins | 252/8.8 |
| 3,654,166 | 4/1972 | Eckert | 252/117 |
| 4,704,226 | 11/1987 | Naylor | 252/162 |

*Primary Examiner*—Paul Lieberman
*Assistant Examiner*—Kathleen Markowski
*Attorney, Agent, or Firm*—Oblon, Spivak, McClelland, Maier & Neustadt

[57] ABSTRACT

N-polyhydroxyalkyl fatty acid amides are used as thickening agents for liquid aqueous surfactant systems. Compounds of formula

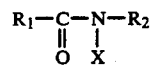

where $R_1$ is an alkyl group; $R_2$ is hydrogen, an alkyl group, or an alkylene oxide group; and X is a polyhydroxyalkyl group, are used as thickeners. The thickeners are particularly useful in liquid surfactant systems which contain paraffinsulfonate.

9 Claims, 2 Drawing Sheets

USE OF N-POLYHYDROXYALKYL FATTY ACID AMIDES AS THICKENING AGENTS FOR LIQUID AQUEOUS SURFACTANT SYSTEMS

This application is a continuation of application Ser. No. 149,479, filed on Jan. 28, 1988, now abandoned.

BACKGROUND OF THE INVENTION

1. Field of the Invention

The invention is directed to the use of N-polyhydroxyalkyl fatty acid amides as thickening agents for liquid aqueous surfactant systems.

2. Discussion of the Background

The volume of production of liquid products in the cosmetics and detergents sector is continually increasing. In recent years the following products have particularly increased in importance: liquid shampoos, bubble baths, and shower preparations, i.e. liquid soaps for use in dispensers which deliver soap to the hand. Liquid dish washing detergents and liquid fine fabric detergents have also acquired substantial markets.

Any useful liquid surfactant formulation must meet the requirement of good shelf life. The liquid should not become turbid or produce sedimentation when subjected to temperature fluctuations. The product should have minimum tendency to have a defatting action on skin, and should not irritate skin.

A liquid surfactant system should have a viscosity which is suited to the intended application, and should be variable over as wide a range as possible.

Thus, viscosity is an important criterion for the quality of a liquid surfactant preparation. For example, for a douche gel one requires a very high viscosity, whereas for a shampoo one ordinarily desires a relatively liquid behavior with relatively low viscosity (1000–4000 mPa-sec).

Known thickeners for liquid surfactant formulations include, among others, nonionic fatty acid polyalkylene glycol esters, such as Antil ® (molecular weight about 3000; provided by the firm Goldschmidt AG), as well as nonionic fatty acid alkanolamides, which have been used for many years (see 1958 *J. Am. Oil Chemists' Soc.*, 35, 548). The preferred fatty acid alkanolamide is coconut oil fatty acid diethanolamide (Superamide ®), which has thickening properties which are superior to those of other fatty acid diethanolamides.

The degree of thickening depends strongly on the surfactant system and on the electrolytes added. Thus, for example, it is known that when secondary paraffinsulfonates are employed as surfactants in liquid preparations, problems are presented in adjusting the viscosity. The known commercially available thickeners mentioned above have insufficient thickening action in systems with secondary paraffinsulfonates in the presence of electrolytes. Viscosity adjusting problems also occur when surfactant mixtures containing paraffinsulfonates are employed as often recommended, e.g. paraffinsulfonate with ether sulfate. See 1976, *Fette—Seifen—Anstrichmittel*, 78, 200.

SUMMARY OF THE INVENTION

Accordingly, one object of the present invention is to provide a thickener for liquid aqueous surfactant systems which satisfies the practical requirements of surfactant, electrolyte, and application.

Another object of the invention is to provide a thickener which gives good results in the presence of secondary paraffinsulfonates as surfactants.

These and other objects which will become apparent from the following specification have been achieved by the present liquid aqueous surfactant composition comprising (a) an aqueous liquid surfactant, and (b) an N-polyhydroxyalkyl fatty acid amide of the formula:

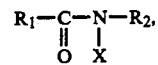

where $R_1$ is an alkyl group, optionally branched, with 1–17, preferably 7–17 carbon atoms;

$R_2$ is hydrogen, or an alkyl group, optionally branched and/or unsaturated, with 1–18, preferably 1–6 carbon atoms, or a group

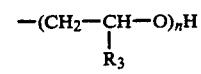

with $n = 0$ to 5, and $R_3$ is hydrogen or —CH$_3$; and

X is a polyhydroxyalkyl group with 4–7 carbon atoms, which may be glycosidically linked with a mono-, di-, or oligosaccharide group.

Figure 1:
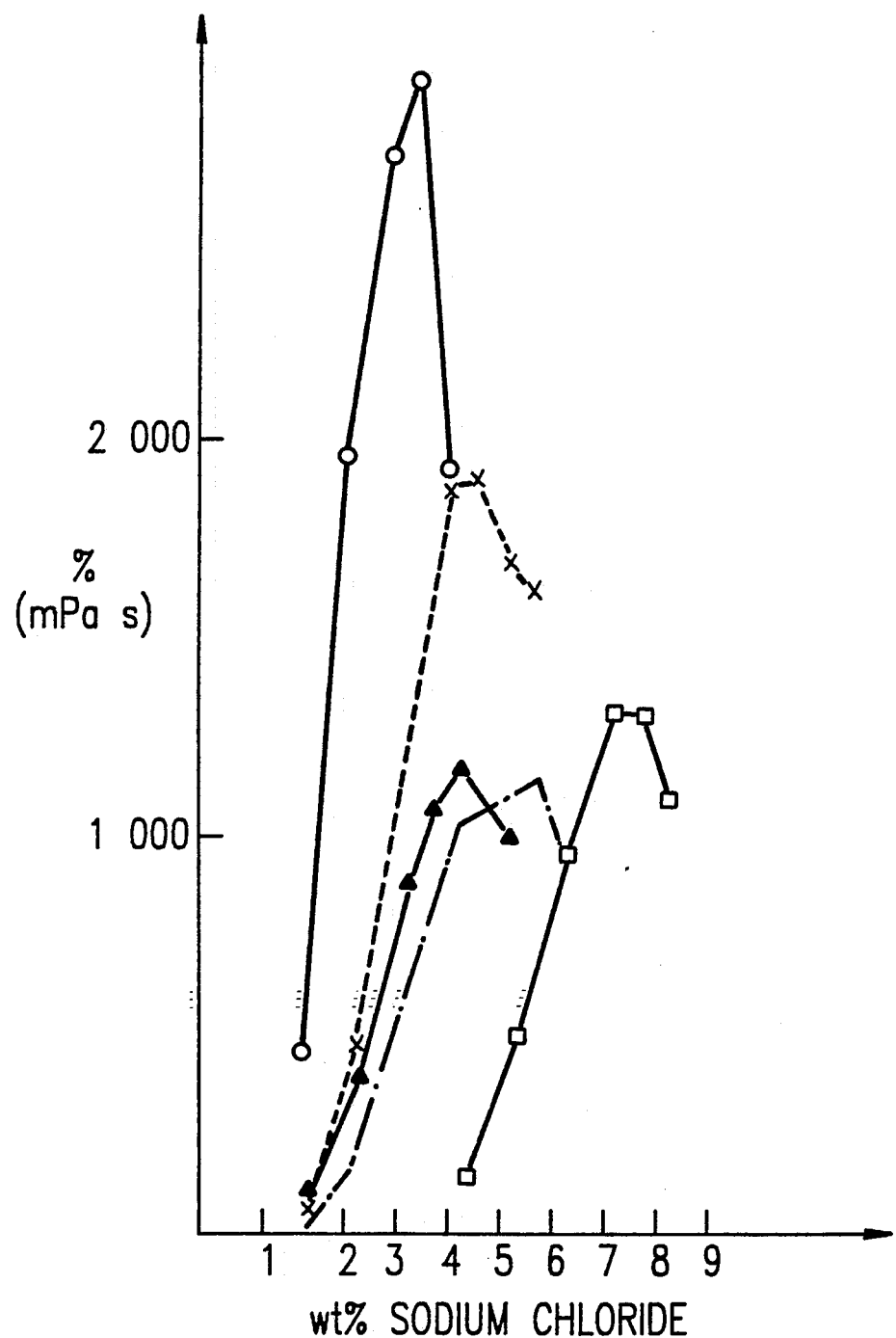
FIG. 1 shows the effect of N-methyl coconut oil fatty acid glucamide and sodium chloride. Concentration of surfactant (10% by wt. in H$_2$O), 3 parts by wt. ether sulfate, 1 part by wt. paraffin sulfonate. The data points indicated by squares show a composition without fatty acid amide. The dotted line shows 3% coconut oil fatty acid diethanolamide. The trianges show 5% coconut oil fatty acid diethanolamide. The crosses show 3% N-methyl coconut oil fatty acid glucamide. The circles show 5% N-methyl coconut oil fatty acid glucamide.

$R_2$ is hydrogen, or an alkyl group, optionally branched and/or unsaturated, with 1–18, preferably 1–6 carbon atoms, or a group with $n = 0$ to 5, and $R_3$ is hydrogen or —CH$_3$; and X is a polyhydroxyalkyl group with 4–7 carbon atoms, which may be glycosidically linked with a mono-, di-, or oligosaccharide group.

DETAILED DESCRIPTION OF THE PREFERRED EMBODIMENTS

The inventively employed N-polyhydroxyalkyl fatty acid amides should be present in an amount of 0.5–30 wt.%, preferably 0.5–10 wt.%, based on the weight of the entire liquid surfactant system.

They may possibly be employed in combination with known thickeners.

In general formula I, the alkyl group $R_1$ may be derived from, e.g., the following carboxylic acids: octanoic acid, decanoic acid, lauric acid, myristic acid, palmitic acid, and stearic acid.

Also in formula I, $R_2$ may be, e.g., methyl, ethyl, n-propyl, isopropyl, n-butyl, isobutyl, n-pentyl, isopentyl, n-hexyl, isohexyl, n-octyl, 2-ethylhexyl, n-nonyl, isononyl, n-decyl, isodecyl, dodecyl, tridecyl, tetradecyl, hexadecyl, stearyl, 2-hydroxyethyl, or 2-hydroxypropyl.

X may be the following polyhydroxyalkyl groups: 1-desoxyerythrityl, 1-desoxyarabityl, 1-desoxyxylityl, 1-desoxysorbityl, 1-desoxysorbit-2-yl, 1-desoxymannityl, 2-desoxymannit-2-yl, 1desoxygalactityl, 1-desoxy-4-glucosido-sorbityl, 1-desoxy-4-galactosido-sorbityl, 2-desoxy-4-glucosido-sorbit-2-yl, 2-desoxy-4-glucosidomannit-2-yl, 1-desoxy-4-maltoglucosido-sorbityl, 1-desoxy-4-oligoglucosido-sorbityl, 1-desoxy-4-polyglucosidosorbityl. X is preferably a 1-desoxysorbityl group.

The following compounds are candidates as inventively employed thickeners: N-methyl coconut oil fatty acid glucamide, stearic acid lactamide, N-methyloleic acid maltamide, N-(2-hydroxyethyl)-lauric acid xylamide, N-ethylmyristic acid galactamide, N-lauryl-N-(4-oligoglucosidosorbityl)-decanoamide, and N-propyl-N-(2-desoxysorbit-2-yl)decanoamide.

Examples of surfactants which may be present in the liquid aqueous surfactant systems are:
(a) anionic surfactants, e.g. alkylarylsulfonates, particularly alkylbenzenesulfonates, olefinsulfonates, secondary paraffinsulfonates, sulfosuccinic acid half ester salts, fatty alcohol ether sulfates;
(b) nonionic surfactants, e.g. fatty alcohol polyglycol ethers, alkylphenol polyglycol ethers, fatty acid polyglycol esters, polypropylene oxide/polyethylene oxide mixed polymers; etc.

An important advantage of the inventively employed class of compounds over currently employed fatty acid diethanolamides is their high adaptability to being adjusted to the given requirements of the surfactant system, by variation of the three substituents $R_1$, $R_2$, and X.

Whereas in the ordinarily employed fatty acid diethanolamides only the alkyl chain of the fatty acid is variable, in the present class of materials there is variability of the hydrophobic N-substituent $R_2$ and the hydrophilic carbohydrate group X, as well as of the fatty acid alkyl chain $R_1$. This enables the thickener to be carefully matched to the liquid surfactant system.

Compounds of formula I are prepared by known means, by reacting fatty acids or fatty acid esters with polyhydroxyalkylamines (which may be N-substituted), in the melt, possibly in the presence of alkaline catalysts.

The polyhydroxyalkylamines are themselves prepared by the widely known method of reductive amination of sugar derivatives using liquid ammonia or other alkylamines (e.g. methylamine, ethylamine, octylamine, laurylamine, coconut oil fatty acid amine, stearylamine, or the alkanolamines, ethanolamine and isopropanolamine). Examples of possible sugar derivatives are: erythrose, arabinose, glucose, galactose, mannose, fructose, xylose, maltose, lactose, saccharose, cellobiose, maltotriose, maltodextrin, and other breakdown products of starch, e.g. glucose syrup.

Other features of the invention will become apparent in the course of the following descriptions of exemplary embodiments which are given for illustration of the invention and are not intended to be limiting thereof.

EXAMPLES

Preparation of N-Methyl coconut oil fatty acid glucamide

In a stirred flask, 669 g (3.0 mol) coconut oil fatty acid methyl ester and 585 g (3.0 mol) N-methylglucamine were heated with gradual addition of 3.3 g sodium methanoate at 135° C. The methanol formed during the reaction was condensed in a cooled receiver under vacuum increasing from 100 to 15 mbar. After methanol evolution ceased, the reaction mixture was dissolved in 1.5 liter hot isopropanol, filtered, and crystallized. After filtration and drying, 882 g (72% of theoretical) of waxy N-methyl coconut oil fatty acid glucamide was obtained. Softening point: 80°–84° C. Base number: 4 mg KOH/g.

The following fatty acid glucamides were prepared analogously:

TABLE I

| | Yield | Softening point (°C.) | Base number (mg KOH/g) |
|---|---|---|---|
| N-methyllauric acid glucamide: | 76% | 94–96 | 6 |
| N-methylmyristic acid glucamide: | 75% | 98–100 | 3 |
| N-methylpalmitic acid glucamide: | 75% | 103–105 | 5 |
| N-methylstearic acid glucamide: | 84% | 96–98 | 6 |

Viscosity Behavior of Surfactant Solutions in the Presence of Thickeners

The measurements were carried out for N-methyl coconut oil fatty acid glucamide.

As a Comparison Example, a thickener according to the prior art was used, e.g. coconut oil fatty acid diethanolamide (Marlamid DF 1218 ®) provided by Huels AG), or the commercial product Antil 141 ®, a polyoxyethylene propylene glycol dioleate, provided by the firm Goldschmidt.

The same technique was used for all the viscosity measurements.

Measuring apparatus: Rotovisco RV 12, computer controlled, supplied by the firm Haake.
Measuring system: MV D1N.
Range of shears: 0–50 sec$^{-1}$.
Temperature: 25° C.
Surfactant, and concentration:
10% mixture of 3 parts fatty alcohol ether sulfate (MARLINAT 24/28 ® Huels AG); and 1 part paraffinsulfonate (MARLON PS 60 ®. Huels AG).

The N-methyl coconut oil fatty acid glucamide had the following formula:

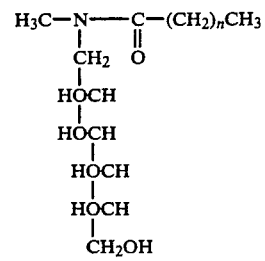

where n=6 to 16.

Coconut oil fatty acid diethanolamide gave better results in an ether sulfate/paraffin sulfate mixed system as shown in FIG. 1.

Figure 2:
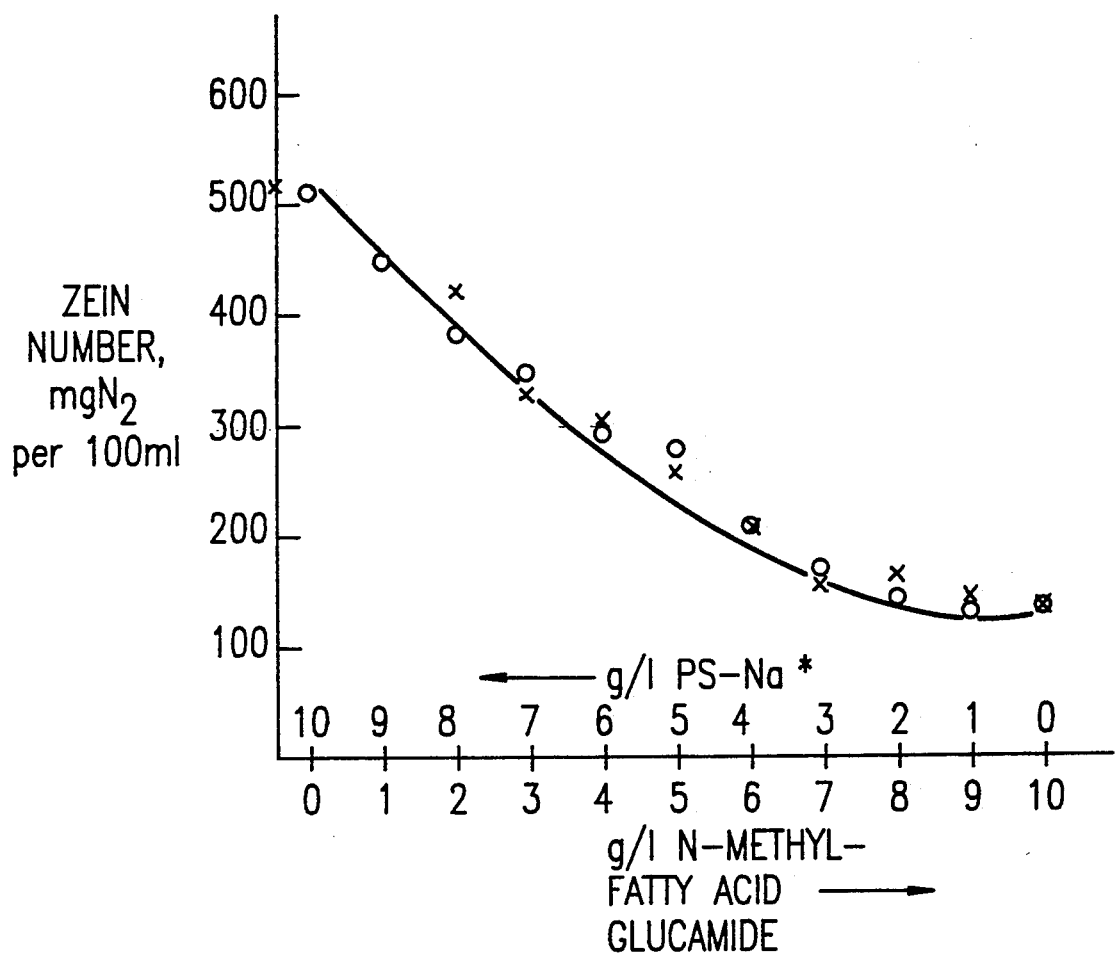
FIG. 2 illustrates the gentleness to skin of mixtures of paraffin sulfonate and N-methyl coconut oil fatty acid (x . . . x) and N-methyl lauric acid glucamide (o . . . o). Zein test according to Goette.

In a shampoo formula with the glucamine salt of paraffinsulfonic acid as the main surfactant, which is particularly gentle to skin, N-methyl coconut oil fatty acid glucamide had a surprising synergistic effect in combination with the known thickener Antil 141 ® (supplied by Goldschmidt AG) which has no thickening action when used alone or with coconut oil fatty acid diethanolamide in a system with paraffinsulfonate salts (see Table II). Formulations with fatty acid glucamides have good shelf life. The compatibility of paraffinsulfonates with human skin is substantially improved by addition of fatty acid glucamides (see FIG. 2).

TABLE II

Shampoo formulations based on a paraffinsulfonic acid sodium salt or a paraffinsulfonic acid glucamine salt (which is gentle to skin), in combination with mixtures of thickeners

| Formula | I (%) | II (%) | III (%) |
|---|---|---|---|
| Paraffinsulfonic acid, glucamine salt | 13.5 | 13.5 | 13.5 |
| Marlamid ® (coconut oil fatty acid diethanolamide | | 3.0 | |
| N-methyl coconut oil fatty acid glucamide | | | 3.0 |
| Antil ® (polyoxyethylene-propylene glycol dioleate | 2.56 | 2.56 | 2.56 |
| Viscosity (mPa.S) | 142 | 317 | 1,590 |
| Paraffinsulfonic acid, sodium salt | 13.5 | 13.5 | 13.5 |
| Marlamid ® | | 3.0 | |
| N-methyl coconut oil fatty acid glucamide | | | 3.0 |
| Antil ® | 2.56 | 2.56 | 2.56 |
| Viscosity (mPa.S) | 63 | 217 | 622 |

The tests clearly show the superiority of the inventively employed N-polyhydroxyalkyl fatty acid amides over conventional thickeners, not only in thickening action but also in gentleness to skin.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A method of shampooing which comprises:
   (1) applying a mixture comprising at least one anionic or nonionic surfactant, water and 0.5–30 wt.% of an N-polyhydroxylalkyl fatty acid amide of formula

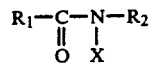

wherein $R_1$ is a branched or straight chain $C_{1-17}$ alkyl group; $R_2$ is hydrogen or a branched or straight chain $C_{1-18}$ alkyl group or a group

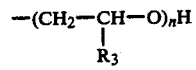

wherein n is 0 to 5, $R_3$ is hydrogen or methyl; and X is a $C_{4-7}$ polyhydroxyalkyl group.

2. The method of claim 1, wherein $R_2$ is a $C_{1-6}$ alkyl group.

3. The method of claim 1, wherein said polyhydroxyalkyl group is glycosidically bonded with a mono-, di-, or oligasaccharide group.

4. The method of claim 1, wherein X is a 1-desoxysorbityl group.

5. The method of claim 1, wherein $R_1$ is a $C_{1-6}$ alkyl group.

6. The method of claim 1, wherein said mixture comprises at least one secondary paraffinsulfonate.

7. The method of claim 1, wherein said N-polyhydroxyalkyl fatty acid amide is a member selected from the group consisting of N-methyl coconut oil fatty acid glucamide, stearic acid lactamide, N-methyl-oleic acid maltamide, N-(2-hydroxyethyl)-lauric acid xylamide, N-ethyl-myristic acid galactamide, N-lauryl-N-(4-oligo-glucosido-sorbityl)-decanoamide, and N-propyl-N-(2-desoxysorbit-2-yl)-decanoamide.

8. The method of claim 1, wherein said anionic surfactant is a member selected from the group consisting of alkylarylsulfonates, olefinsulfonates, sulfosuccinic acid half ester salts, and fatty alcohol ether sulfates.

9. The method of claim 1, wherein said nonionic surfactant is a member selected from the group consisting of fatty alcohol polyglycol ethers, alkylphenol polyglycolethers, fatty acid polyglycol esters, and polypropylene oxide/polyethylene oxide mixed polymers.

* * * * *